United States Patent [19]
Galzy et al.

[11] 3,981,773
[45] Sept. 21, 1976

[54] PROCESS FOR THE PREPARATION OF GALACTOSE AND BEVERAGES BASED ON GALACTOSE FROM SOLUTIONS CONTAINING LACTOSE

[75] Inventors: Pierre Galzy; Guy Jean Moulin, both of Montpellier, France

[73] Assignee: Agence Nationale de Valorisation de la Recherche (ANVAR), Neuilly sur Seine, France

[22] Filed: July 18, 1974

[21] Appl. No.: 489,736

[30] Foreign Application Priority Data
July 20, 1973 France ............................ 73.26663
Aug. 3, 1973 France ............................ 73.28537

[52] U.S. Cl. ............................... 195/31 R; 195/79; 426/34; 426/42; 426/43; 426/48
[51] Int. Cl.² ..................... C12D 13/02; C12K 1/02
[58] Field of Search ................. 195/31 R, 82, 7, 11, 195/96, 81, 46, 79, 76, 77, 78, 961; 426/48, 42, 43, 34

[56] References Cited
UNITED STATES PATENTS

| | | | |
|---|---|---|---|
| 2,826,502 | 3/1958 | Sfortunato et al. | 195/11 |
| 2,826,503 | 3/1958 | Roberts et al. | 426/42 |
| 3,753,725 | 8/1973 | Williams et al. | 195/11 |

OTHER PUBLICATIONS

Chem. Abstracts, 72:29143w.
Chem. Abstracts, 73:129742e.

Primary Examiner—A. Louis Monacell
Assistant Examiner—Thomas G. Wiseman
Attorney, Agent, or Firm—Donald D. Jeffery

[57] ABSTRACT

A process for the preparation of galactose which comprises (1) the cultivation of a mutant, non-pathogenic protoprophic yeast or bacteria possessing $\beta$-galactosidase activity and a gal⁻ character on a media containing lactose, e.g., lactoserum and (2) recovery of the galtose. The mutants are produced using two different methods. The galactose solutions produced are suitable for use in beverages.

14 Claims, No Drawings

PROCESS FOR THE PREPARATION OF GALACTOSE AND BEVERAGES BASED ON GALACTOSE FROM SOLUTIONS CONTAINING LACTOSE

This invention relates to a process for the preparation of galactose and beverages based on galactose from solutions containing lactose.

This process is particularly suitable for use in the dairy industry, especially for the treatment of lactoserum used in the form of a solution of lactose.

BACKGROUND OF INVENTION

The dairy industry is producing increasing quantities of lactoserum which is a liquid phase obtained after the precipitation from milk (by the addition of rennet or acid) of the casein used in the production of cheese. Lactoserum has the following average composition.

| | | |
|---|---|---|
| water | 960 | g |
| lactose | 35 | g |
| ash | 4 | g |
| potassium | 1 | g |
| sodium | 0.50 | g |
| riboflavin | 1.4 | mg |
| niacin | 1 | mg |
| thiamin | 0.3 | mg |
| calcium | 0.25 | mg |
| phosphorus | 0.20 | mg |
| vitamin A | 100 UI | |
| proteins | traces | |

French Pat. 71 27592 describes a process for the preparation of galactose from a solution of lactose such as lactoserum. In this process, it is first of all necessary to bring the lactose concentration of the lactoserum to between 5 and 15%, then to subject the solution obtained to acid hydrolysis, followed by adjustment of the pH of the solution to a value between 3 and 6. The solution, which now contains glucose and galactose emanating from the hydrolysis of lactose, is fermented by a strain of fermenting yeast which assimilates the glucose but not the galactose. The yeasts are then separated from the medium containing the galactose by centrifuging.

The process involves numerous operations. It is possible by chemical hydrolysis to treat lactose solutions with a concentration of from 5 to 15%, whereas crude lactoserum only contains approximately 3.5% of lactose. As a result, it is difficult to obtain the complete removal of glucose in the fermentation towers. In addition, since the operation is carried out without growth, it requires particular sterility conditions.

SUMMARY OF INVENTION

The present invention relates to a process for the treatment of solutions containing lactose, in particular, lactoserum or milk with microorganisms to produce, on the one hand, a mass of microorganisms which can be used in the feeding of animals and, on the other hand, a solution of galactose which can be directly used after clarification for the preparation of beverages. If desired, it is also possible by the process according to the invention to prepare galactose by extraction from its solution.

Although the starting products used for the present process are not limited to lactoserums, the use of lactoserums as starting materials does have numerous advantages.

Thus, lactoserum is currently a fairly strong pollutant of the waterways into which it is discharged from dairies, because hitherto it has only been a by-product of no commercial value. By virtue of the present invention, it is possible to obtain interesting, directly marketable products from lactoserum, and to eliminate the need to discard lactoserum, which is doubly advantageous.

On the other hand, certain people, in particular the aged and certain adults, lose their ability to hydrolyse the lactose in their food as a result of a reduction in the secretion of $\beta$-galactosidase. The major consequence of this phenomenon, which is widespread in Africa, Asia and the Mediterranean countries, is that the people affected by it are deprived of an essential sugar, namely galactose, which emanates almost exclusively in nutrition from the in vivo hydrolysis of the lactose present in milk.

Accordingly, it is advantageous that there should be a dietetic milk entirely assimilable by people affected by the enzymatic deficiency referred to above and containing galactose.

Apart from the fact that it eliminates the need for most of the operations referred to above, the process according to the invention has other advantages which will become apparent from the following description.

According to the invention, galactose or a beverage containing galactose is prepared from a solution containing lactose, in particular lactoserum or milk, by treating the lactose-containing solution with a mutant, non-pathogenic, prototrophic microorganism which contains a $\beta$-galactosidase and which has a gal$^-$ character, i.e., is incapable of fermenting galactose, subsequently separating the microorganisms with the solution containing galactose, if desired after fermentation, and, if necessary, extracting the galactose from this solution.

In one of the preferred embodiments of the invention, the microorganism used in a bacteria obtained by mutation and selection from a wild strain. This bacteria is preferably selected from the Enterobacteriaceae or the Lactobacteriaceae, in particular *Escherichia coli*. The *Escherichia coli* strain is preferably the CBS 6051 B strain lodged in Delft (cf. Example 1).

In another preferred embodiment of the invention, the microorganism used is a yeast. This yeast is obtained by mutation and selection, preferably from a haploid strain, the wild strain preferably being selected from:

The ascomycetes
*Debaryomyces cantarellii*
*Debaryomyces castellii*
*Debaryomyces hansenii*
*Debaryomyces morana*
*Debaryomyces tamarii*
*Hansenula capsulata*
*Kluyveromyces aestuarii*
*Kluyveromyces bulgarious*
*Kluyveromyces cicerisporus*
*Kluyveromyces fragilis*
*Kluyveromyces lactis*
*Kluyveromyces wikerhamii*
*Lipomyces lipofer*
*Lipomyces starkeyi*
*Pichia farinosa*
*Pichia polymorpha*

*Pichia pseudopolymorpha*
*Pichia scolyti*
*Pichiastipitis*
*Schwanniomyces castellii*
*Wingea robertsii*,
in particular the *Kluyveromyces fragilis* or *Kluyveromyces lactis*,
or from:
The basidiomycetes
*Leucosporium frigidum*
*Leucosporidium scottii*
*Bullera alba*
*Bullera strigea*
*Sporobolomyces singularis*.

In another preferred embodiment of the invention, the microorganism used is one of the mutant yeasts of *Kluyveromyces fragilis* lodged at the Central Bureau voor Schimmelcultures in Delft under the Nos. CBS 6498 and 6499.

In one variant of the process according to the invention, proteins are removed from the lactoserum before fermentation by any of the well-known processes, such as hot precipitation of the proteins in acid medium or by ultrafiltration on a selective membrane.

Separation of the microorganisms after fermentation can be carried out by any known method, in particular by centrifuging. In the case of yeasts, the use of these microorganisms in nutrition does not involve any problems, because the by-product in question is one which has a certain economic interest. In the case of bacteria, they may optionally be used in the feeding of poultry.

In cases where yeasts are used, and providing the fermentation medium is strongly aerated, no by-product is left in the solution which, therefore, can be directly used in the preparation of beverages containing galactose.

If necessary, fermentation can also be stopped before all the lactose has been consumed, so as to obtain a solution of lactose and galactose.

If the lactose solution is a milk (whole milk, semi-skimmed milk or skimmed milk) the dietetic milk obtained after separation of the mass of yeasts is directly marketable, because the yeasts do not leave any residues in the fermentation solutions. However, the present invention also relates to a process, and to a product obtained by this process, in which following separation, glucose or saccharose is added to the milk before conditioning. Thus, in the context of the invention, hydrolyzed lactose milk is a milk free from lactose, or contains a reduced quantity of lactose and contains at least either galactose, or galactose and glucose, or galactose and saccharose.

It is also possible by the process according to the invention to obtain a milk enriched in proteins by carrying out only a partial separation of the yeasts, or even by carrying out no separation at all. In this way, the milk is left with yeasts in suspended form so that it is rich in proteins. The milk thus obtained is preferably packaged in powder form.

In the context of the invention, treatment of the lactose solution obviously means the inoculation and fermentation which are carried out by well-known methods.

In cases where bacteria, in particular coliform bacteria, are used, the fermentation process is more rapid and does not necessitate as much aeration as in the case of yeasts, which is an advantage, although on the other hand the fermentation medium is left with by-products that are not exactly favourable to the preparation of beverages, with the result that it is generally preferred in this case to extract the galactose from the solution, for example by concentrating the solution obtained until a 50% dry extract is obtained, crystallizing by cooling to around 20°C after washing, centrifuging and decantation. The product can be spray-dried or, in order to obtain a higher degree of purity, it can be dissolved in hot water and then passed over active carbon, followed by crystallization, washing, centrifuging, decantation and spray-drying or fluidized-bed drying, followed by grinding in a mill. Alternatively, the pure galactose can be obtained by extraction with a solution of ethyl alcohol in accordance with a well-known process.

There is illustrated below the scheme of the probable metabolism of galactose in microorganisms and its relationship to the invention. In certain yeasts and certain bacteria, lactose is hydrolyzed by a β-galactosidase, but the microorganisms which contain this β-galactosidase also possess in general the enzymatic equipment for metabilizing the galactose. The scheme of the metabolism of galactose in microorganisms is as follows:

First stage:
Penetration of galactose through a permease.
Second stage:

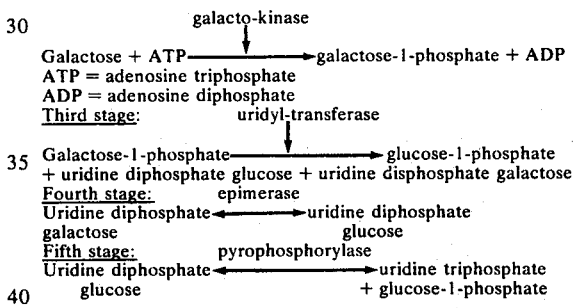

ATP = adenosine triphosphate
ADP = adenosine diphosphate

Third stage: uridyl-transferase

Galactose-1-phosphate ⟶ glucose-1-phosphate
+ uridine diphosphate glucose + uridine disphosphate galactose Fourth stage: epimerase
Uridine diphosphate ⟷ uridine diphosphate
galactose                         glucose Fifth stage: pyrophosphorylase
Uridine diphosphate ⟷ uridine triphosphate
glucose                          + glucose-1-phosphate Genetic studies have shown that these various stages are controlled by a single enzyme and hence by a single gene, a mutation at gene level controlling one of the following enzymes: permease, galacto-kinase, uridyl-transferase or epimerase, thus precludes the use of galactose. It is thus possible to produce a strain containing a β-galactosidase and having lost by mutation an enzyme indispensable for the use of the galactose liberated in the cell. However, the mutation preventing the use of permease cannot be used in the process according to the invention, because the microorganism remains capable of metabolizing the galactose when the galactose is already present inside the cell, which is the case during the hydrolysis of lactose. The most interesting mutation for the use of the strain in the process according to the invention is the loss of uridyl-transferase.

Two different types of mutation and selection can be used for obtaining bacterial strains suitable for use in the process according to the invention.

The first method, which starts with a strain of a collection having the gal⁻ character and a β-galactosidase, this strain being non-pathogenic, but auxotrophic to certain substances, comprises treating this strain in such a way as to reverse it for its various auxotrophs until a prototrophic strain which has retained its other characteristics is obtained. On an industrial level, a prototrophic strain has the advantage of not necessitating the addition of growth factors which are necessary to the development of an auxotrophic strain.

The following technique is one example of a process for reversing an auxotrophic strain:

Starting with a culture of the auxotrophic strain, prepared naturally in a medium containing the growth factors, $10^8$ to $10^9$ cells are spread over the surface of a minimum medium (one of the characteristics of a prototrophic strain of course is that all its constituents can be synthesized in an exclusively mineral synthetic medium known as the minimum medium), from which a growth factor X necessary to the growth of the starting strain is missing. The reversed mutant which has become prototrophic for the factor X then grows.

The cultures are then spread over the surface of a medium accommodated in a Petri dish. The colonies appearing are isolated and sampled. They have become prototrophic for the factor X and can be used in another stage of the process in which they will be reversed for another of the auxotrophs of the initial strain.

It is by this process that we have prepared the mutant which is the subject of Example 1 below.

It is also possible to obtain from a wild strain a bacterial strain which can be used in the process according to the invention by another mutation-selection process. The description of this process, given below with reference to *Escherichia coli*, can of course be used for other wild strains, in particular for strains of Enterobacteriaceae or Lactobacteriaceae.

*Escherichia coli* belongs to the family of Enterobactericeae and to the tribe of Escherichiaceae, which are gram-negative bacteria cocoid or slightly elongate in shape. The cells are isolated in pairs or in short chains, generally without a capsule and, in most cases, mobile, which are optional anaerobes showing a fermentation of glucides of the mixed acid type, without any acetoin being formed, and reacting positively to a methyl red test. These bacteria use the glucides, in particular lactose, galactose, glucose and mannitol, they possess the lysine decarboxylase, but do not give phenylpyruvic acid from phenylalanine; they no longer hydrolyze urea and do not give off $H_2S$.

The wild strain of *Escherichia coli* is treated with a physical or chemical mutagen in order to increase mutation frequency for the genes involved in the metabolism of galactose. Examples of physical mutagens include ultraviolet rays, x-rays and gamma rays, whilst chemical mutagens include ethylmethane sulphonate, nitrous acid, alkylating agents, nitrosoguanidine, acryflavin or other compounds well known as mutagens.

This treatment is followed by enrichment in mutant bacteria having the gal⁻ character. To this end, the population which has undergone mutation is transferred to another medium allowing growth in which the only carbon source is galactose and which additionally contains an antibiotic, such as penicillin. The antibiotic kills the cells in the process of vegetative multiplication, but has no effect upon the mutants incapable of multiplying through their inability to metabolize galactose. After a certain time, only those bacteria which have a gal⁻ character are left. The isolated strains have to be subjected to another selection because some of the strains obtained, although incapable of using galactose as carbon source, cannot be used in the process according to the invention. These strains are, for example, strains which do not possess the permease.

In order to eliminate these undesirable strains, the strains obtained in the preceding stage are cultured in a Petri dish containing a complete medium based on glucose as carbon source. It is advisable to spread approximately 100 living cells per dish. The colonies which appear are replicated by "replicaplating" (for culture by replication) in a medium based on galactose. The required gal⁻ mutants give colonies in the first medium based on glucose, but not in the medium based on galactose.

Among the mutant gal⁻ lactose⁺ clones, it is advisable to select, through suitable tests, those which are able to hydrolyze the lactose while rejecting the galactose in the medium.

In every case, it is possible to make acellular preparations and to dose the enzymatic activities in order to determine what the missing enzyme is for each clone.

In cases where it is desired to use a yeast as microorganism in accordance with the invention, the process of mutation and selection of the yeast is the following, the following description being given with reference to the strain *Kluyveromyces fragilis*, but is also applicable to other yeast strains, in particular to those which belong to the ascomycetes and which are heterothalic diplobiontics, more especially those mentioned above. It is also possible to use certain basidiomycetes, more especially the strains referred to above.

Finally, it is possible to use yeasts belonging to the fungi-imperecti, although it is more difficult to obtain defective mutants for galactose and utilizing lactose in the case of these yeasts because their biological cycle is unknown and it is not known whether they are haploids or diploids. Yeasts of this type particularly suitable for use in the process according to the invention are the following:

*Brettanomyces anomalus*
*Brettanomyces claussenii*
*Brettanomyces curtersii*
*Candida aaseri*
*candida aquatica*
*Candida blankii*
*Candida curvata*
*Candida glaebosa*
*Candida humicola*
*Candida intermedia*
*Candida kefyr*
*Candida macedoniensis*
*Candida muscorum*
*Candida pseudotropicalis*
*Candida salmanticensis*
*Candida shehatae*
*Candida tenuis*
*Cryptococcus albidus*
*Cryptococcus ater*
*Cryptococcus dimennae*
*Cryptococcus flavus*
*Cryptococcus gastricus*
*Cryptococcus hungaricus*
*Cryptococcus infirmo-miniatus*
*Cryptococcus laurentii*
*Cryptococcus macerans*
*Cryptococcus melibiosum*
*Cryptococcus terreus*
*Rhodotorula aurantiaca*
*Rhodotorula lactosa*
*Rhodotorula marina*
*Rhodoturula minuta*
*Sterigmatomyces halophilus*

*Torulopsis candida*
*Torulopsis ingeniosa*
*Torulopsis versatilis*
*Trichosoporum cutaneum*
*Trichosporum inkin*
Trichosporum pullulans.

The strain *Kluyveromyces fragilis* occurs in nature in diploid form. However, the search for mutants for a given gene can only be made with reasonable chances of success from an individual haploid. The process for obtaining a strain suitable for use in the process according to the invention is therefore in two main parts. The first is the search for individual haploids, whilst the second is the mutation and selection of the haploid strains obtained.

The description of the species according to J. Lodder is given below:

| Assimilation of carbon-containing substrates: | | | | | |
|---|---|---|---|---|---|
| Glucose | + | melezitose | − | ribitol | ± |
| Galactose | + | inulin | + | galactitol | − |
| L.sorbose | ± | D-xylose | + | D-mannitol | + |
| Sucrose | + | L-arabinose | + | D-glucitol | + |
| Maltose | − | D-arabinose | − | α-methyl-D-glucoside | − |
| Cellobiose | + | D-ribose | ± | salicin | + |
| Threhalose | − | L-rhamnose | − | lactic acid DL | + |
| Lactose | + | ethanol | + | succinic acid | + |
| Melibiose | − | glycerol | + | citric acid | ± |
| Raffinose | + | erythritol | − | inositol | − |
| Fermentation of carbon-containing compounds: | | | | | |
| Glucose | + | melibiose | − | melezitose | − |
| Raffinose | + | saccharose | + | cellobiose | − |
| Maltose | − | inulin | + | α-methyl-D-glucoside | − |
| Lactose | + | galactose | + | trehalose | − |

Other tests
  Hydrolysis of arbutin,
  assimilates the nitrates of potassium and ethylamine hydrochloride as nitrogen source,
  negative growth in the absence of vitamins,
  growth at 37°C,
  resistant to cycloheximine
Growth on malt extract After 3 days at 28°C, the cells are ellipsoidal or cylindrical $(2.0 - 6.0) \times (3.5 - 10.0)$ μ. They are single, in pairs or in chains. The pseudomyceliums are formed in a more or less large quantity. A button appears and occasionally a ring.

After a month at ambient temperature, a large button has formed. A ring is normally present.
Growth on a gelose-containing malt extract After 3 days, the cells are cylindrical or ellipsoidal; in most cases single in pairs or in short chains. A pseudomycelium is frequently formed. The culture is bright cream color. The colonies are smooth or sometimes plaited.
Formation of ascospores The diploid cells are directly transformed into asci. There can be conjugation between isolated cells. Somatogamy can precede formation of the ascus. One to four spores are formed per ascus. The ascospores are quickly released into the medium and agglutinate. The ascospores are reniform or elongate.
Formation of pseudomycelliums A pseudomycelium is formed in the special media. It develops better in anaerobiosis. It can be rudimentary or branched.

In order to obtain haploid clones, the strain is grown in a rich medium (yeast extract, glucose, peptone). The culture in its exponential growth phase is transferred to a sporulation medium whose composition is described by F. Vezinhet: it is a mixture of equal parts of a 0.4 M potassium acetate solution and Sorensen M/15 phosphate buffers (pH 7).

After 48 to 72 hours, 80% of the cells have sporulated. The asci burst very rapidly and release the haploid spores into the medium. The standard technique using Fontbrune's micromanipulator cannot be used in this case because the spores are 99% lethal. Heat treatment has to be applied in order to obtain haploid clones because the vegetative cells are less resistant to heat than the spores, and treatment for 2 minutes at 60°C destroys 99% of the vegetative diploid forms. Following this treatment, colonies are spread over the surface of a rich medium in a Petri dish at the rate of 100 to 200 colonies per dish. The dishes are observed after 48 to 72 hours incubation in an oven at 26°C, and the cellular clones which appear are removed. Each clone is cultured in a rich medium and then tested in a sporulation medium. Each clone which sporulates can be eliminated between it is diploid. Those clones which do not sporulate are assumed to be haploid. In order to confirm the haploid character of each clone, it is necessary to attempt to mark them by auxotrophic mutations. One quick and simple method is to look for the clones which lead to auxotrophic mutants for an amino acid or a base during a mutagenesis. The technique involved comprises allowing a physical or chemical mutagen, such as these described for the mutation of bacteria for example, on a population in the stationary phase. In the present case, it is preferred to use ethylmethane sulphonate. The culture is then transferred to a medium in which only the prototrophs grow, and on which a fungicide is allowed to act after one to two generations. The mycostatin kills the cells in the growth phase which correspond to the prototrophic clones that have not undergone mutation. After dilution, 100 cells per dish are spread over a complete medium in which the auxotrophs are able to develop, after which the dishes are incubated for 48 to 72 hours. By the replicaplating technique, it is then possible to identify those clones which have developed in a complete medium and have not produced colonies in the minimum medium in which only the prototrophs develop. After incubation for 48 hours, it is possible to mark the auxotrophs. This technique enables haploid clones to be obtained.

The strains thus obtained and marked are used in the search, in the following stage, for mutants for one of the genes preventing the utilization of galactose.

The technique of mutation and selection intended for obtaining gal⁻ mutants is the same as that described above for obtaining auxotrophic mutants. Only the culture media are different. The "complete" medium allowing growth will be a medium containing glucose, whilst the "minimum" medium will contain galactose. When, after replicaplating, a certain number of clones do not develop in the minimum medium, they are removed and tested in liquid medium in the following media: yeast extract + galactose, and lactoserum.

Of all the clones which do not grow on galactose, some cannot be used in the process according to the invention. For example, a strain which has muted for permease will not develop on lactose because galactose can only penetrate by osmosis. Nevertheless this strain will consume the lactose following the hydrolysis of lactose, because hydrolysis takes place inside the cell. It is possible to determine the lost enzyme by an enzymatic study. In the same way as for bacteria, when a gal⁻ mutant is marked for an auxotroph, it is necessary to attempt reversion by a technique such as that indicated earlier on. Although the yeast strains thus obtained can be used in the process according to the invention, it is generally preferred to convert these strains into diploids, because diploid strains have a better growth than the haploids.

A certain number of techniques have already been developed with a view to converting haploid strains into diploids. Cells can be crossed individually using a micromanipulator, or alternatively to auxotrophic clones, if necessary complementary cells, can be crossed whilst, at the same time, sifting out the protorophs. It is of course necessary to cross clones with opposite sexual signs. The methodology described can be used for all the cells capable of metabolizing lactose and galactose provided that they are diplobiontic and heterothalic. In the case of haplobiontic yeasts, mutagenesis can be applied directly to collection cells or to cells isolated in nature.

Certain difficulties can arise in the case of homothalic diplobiontic yeasts, such as Kluyveromyces marxianus. After sporulation, the spores can be extracted. Each spore develops to give a haploid clone. The haploid clone subsequently converts into the diploid form without any crossing. The search for mutants is now extremely difficult and the changes of obtaining a mutant with the diploids are extremely low, being of the order of $10^{-14}$ to $10^{-16}$. In this particular case, it has not known whether the clone is a diploid or a haploid.

PREFERRED EMBODIMENTS

The invention is illustrated by the following Examples.

EXAMPLE 1

The process according to the invention is carried out with a bacteria of the *Escherichia coli* type lodged at the Centraal Bureau voor Schimmelcultures in Delft under the Nos. CBS 6051 B obtained by mutation and selection from a strain from the Pasteur Institute in Paris named B 112.21 and catalogued under the No. 115.15. This strain has the following genotype: Thi⁻ gal⁻ (transferase), Hfr P 0.00.

After having obtained reversion of the auxotroph for thymin by the process described above, growth on lactoserum was studied. The precultures were made in a mineral medium complemented with thiamin with the following composition:

| | | |
|---|---|---|
| K₂ H PO₄ | 7 | g/l |
| K H₂ PO₄ | 3 | g/l |
| (NH₄)₂ SO₄ | 1 | g/l |
| Mg SO₄.7 H₂O | 0.10 | g/l |
| Sodium citrate . 2 H₂O | 0.5 | g/l |
| iron citrate | 0.3 | mg/l |
| Mn SO₄.H₂O | 0.17 | mg/l |
| glucose or lactose | 5 | g/l |
| thiamin | 1 | mg/l |

Culturing proper is carried out on lactoserum complemented with thiamin in a quantity of 1 microgram/ml at a temperature of 34°C ± 0.5°C, being accompanied by agitation in order to aerate the medium and to keep the cells in suspension (80 oscillations per minute, oscillation amplitude 7 cm). The culture is inoculated with the preculture in a mineral medium. A population giving around 1.5 to 3.5 mg of dry material per ml of lactoserum is obtained under these conditions. Quantitive analysis of the remaining sugars is carried out by chromatography on Whatman No. 1 paper by Partridge's method. All the chromatographs show the presence of galactose in the medium at the end of growth. It was not possible to detect any trace of glucose. After growth for 48 hours on lactoserum containing 35 g/l of lactose, almost all the lactose had disappeared.

This strain thus effects the required operation and quantitatively hydrolyzes the lactose in the lactoserum into galactose which accumulates in the medium, and into glucose which is consumed.

EXAMPLE 2

In this Example, the process according to the invention is carried out with a yeast *Kluyveromyces fragilis* SG 11 registered at Delft under the No. CBS 6498 and obtained from a *Kluyveromyces fragilis* strain with the name SG 1 lodged under the No. CBS 6497, to which the mutation and selection treatment described above has been applied.

The cultures are made in 5 liter Erlenmeyer flasks filled to 1/10th of their volume with crude lactoserum without any growth factor. The temperature is kept at 26°C ± 0.5°C. The medium is agitated at 80 oscillations per minute, oscillation amplitude 7 cm. In this medium, the strain gives populations of the order of $300 \times 10^6$ cells per ml after 120 hours' growth. This strain consumes all the lactose in a lactoserum containing 35 g/l of lactose. Disappearance of the lactose and the presence of galactose were determined in the medium by the chromatographic method described above for bacteria.

The growth of this strain is complete after 120 hours, but shows a particularly long latency phase of 48 hours.

EXAMPLE 3

The strain used in this Example is a *Kluyveromyces fragilis* SG 12 lodged at Delft under the No. CBS 6499, having been obtained at the same time as SG 11 by mutation-selection from the strain SG 1 of Example 2. The culturing conditions are the same as in Example 2, but the strain SG 12 gives populations of the order of $500 \times 10^6$ cells per ml after 72 hours' growth. It consumes all the glucose corresponding to the hydrolysis of a lactoserum containing 35 g/l of lactose, and quantitatively liberates the galactose into the solution.

The latency phase of the SG 12 strain is only 30 hours. It is possible to eliminate the latency phase. Where culturing is carried out by a continuous technique, the latency phases disappear, but in this case the sterility precautions are more difficult to observe.

Following fermentations in the two preceding cases, the microorganisms are centrifuged, which enables the yeasts or the bacteria on the one hand and the galactose solution on the other hand to be recovered. In the case of yeasts, this solution can be used directly or after concentration for the production of beverages, the yeasts being washed if necessary and then dried under heat and dispersed on a cylinder for example. In the case of bacteria, it is generally necessary to extract the galactose in order to separate the fermentation residues unsuitable for consumption. To this end, the solution is concentrated until a 50% dry extract is obtained, followed by crystallization by cooling to around 20°C. If it is desired to obtain a galactose of the codex type, it may be necessary to repeat crystallization after passage over active carbon or even by extracting the solution with ethyl alcohol.

EXAMPLE 4

A skimmed milk is inoculated with the strain *Kluyveromyces fragilis* No. CBS 6498. After about 72 hours under strong aeration, the yeast population reaches 4 $10^8$ cells/ml. The lactose has completely disappeared from the milk, while the galactose has remained quantitatively intact. The milk containing the galactose (10,000 g) is then centrifuged. The yeasts which constitute a valuable by-product are recovered together with the milk which, although free from lactose, has retained its organoleptic qualities and its galactose. As already mentioned, it is possible completely to restore the milk to its original nutritive value by adding glucose.

EXAMPLE 5

The procedure used is that described in Example 4, except that, instead of being centrifuged, the yeast mass is kept in suspension in the medium, and the milk is packaged in powder form. The milk thus obtained is considerably richer in proteins than ordinary milk.

What is claimed is:
1. A process for the preparation of a solution containing galactose from a solution containing lactose comprising:
   a. inoculating said solution containing lactose with a culture of a living mutant, non-pathogenic, prototrophic yeast having β-galactosidase and gal⁻ character selected from the group consisting of ascomycetes and basidiomycetes;
   b. fermenting said solution to produce a galactose containing solution; and
   c. recovering said galactose containing solution.
2. The process of claim 1, wherein said yeast is a diploid.
3. The process of claim 1, wherein said yeast is obtained by mutation and selection.
4. The process of claim 1, wherein said solution containing lactose is selected from the group consisting of lactoserum, whole milk, semi-skimmed milk and skimmed milk.
5. The process of claim 1, wherein the solution containing lactose is a lactoserum.
6. A process for the preparation of a solution containing galactose, from a solution containing lactose, comprising:
   a. innoculating said solution containing lactose with a culture of a living mutant, non-pathogenic, prototrophic microorganism having β-galactosidase and a gal⁻ character and selected from the group consisting of bacteria selected from Enterobacteriaceae and Lactobacteriaceae and yeast selected from

*Debaryomyces cantarellii*
*Debaryomyces castellii*
*Debaryomyces hansenii*
*Debaryomyces morana*
*Debaryomyces tamarii*
*Hansenula capsulata*
*Kluyveromyces aestuarii*
Kluyveromyces bulgarious
*Kluyveromyces cicerisporus*
*Kluyveromyces fragilis*
*Kluyveromyces lactis*
*kluyveromyces wikerhamii*
*Lipomyces lipofer*
*Lipomyces starkeyi*
*Pichia farinosa*
*Pichia polymorpha*
*Pichia pseudopolymorpha*
*Pichia scolyti*
*Pichia stipitis*
*Schwanniomyces castellii*
*Wingea robertsii*
*Leucosporium frigidum*
*Leucosporidium scottii*
*Bullera alba*
*Bullera strigea*
*Sporobolomyces singularis*
*Brettanomyces anomalus*
*Brettanomyces claussenii*
*Brettanomyces curtersii*
*Candida aaseri*
*Candida aquatica*
*Candida blankii*
*Candida curvata*
*Candida glaebosa*
*Candida humicola*
*Candida intermedia*
*Candida kefyr*
*Candida macedoniensis*
*Candida muscorum*
*Candida pseudotropicalis*
*Candida salmanticensis*
*Candida shehatae*
*Candida tenuis*
*Cryptococcus albidus*
*Cryptococcus ater*
*Cryptococcus dimennae*
*Cryptococcus flavus*
*Cryptococcus gastricus*
*Cryptococcus hungaricus*
*Cryptococcus infirmo-miniatus*
*Cryptococcus laurentii*
*Cryptococcus macerans*
*Cryptococcus malibiosum*
*Cryptococcus terreus*
*Rhodotorula aurantiaca*
*Rhodotorula lactosa*
*Rhodotorula marina*
*Rhodoturula minuta*
*Sterigmatomyces halophilus*
*Torulopsis candida*
*Torulopsis ingeniosa*
*Torulopsis versatilis*
*Trichosporum cutaneum*
*Trichosporum inkin*
*Trichosporum pullulans;*
   b. fermenting said solution to produce a galactose containing solution; and
   c. recovering said galactose containing solution.
7. The process of claim 6 wherein said bacteria is an *Escherichia coli*.
8. The process of claim 7 wherein said bacteria is an *Escherichia coli*, deposited under the number CBS 6051 B at the Centraal Bureau voor Schimmelcultures in Delft, Holland.
9. The process of claim 6, wherein said bacteria is a bacteria obtained from a mutant non-pathogenic auxotrophic bacteria possessing a β-galactosidase and a gal⁻ character which has been reversed for its various auxotrophs.

10. The process of claim 6 wherein said yeast is a diploid.

11. The process of claim 6 wherein said yeast is selected from the *Kluyveromyces fragilis* strains deposited at the Centraal Bureau voor Schimmelcultures in Delft, Holland, under the numbers CBS 6498 and 6499.

12. The process of claim 6 wherein said yeast is obtained by mutation and selection.

13. The process of claim 6 wherein said solution containing lactose is selected from the group consisting of lactoserum, whole milk, semi-skimmed milk and skimmed milk.

14. The process of claim 13 wherein the solution containing lactose is a lactoserum.

* * * * *